United States Patent [19]

Reddy et al.

[11] Patent Number: 4,932,958
[45] Date of Patent: Jun. 12, 1990

[54] PROSTATE BALLOON DILATOR

[75] Inventors: Pratap K. Reddy, Bloomington; Michael A. Mikulich, Shakopee, both of Minn.

[73] Assignee: American Medical Systems, Inc., Minnetonka, Minn.

[21] Appl. No.: 192,432

[22] Filed: May 10, 1988

[51] Int. Cl.$^5$ .................... A61M 29/02; A61M 25/10
[52] U.S. Cl. .................................. 606/192; 604/101; 604/54
[58] Field of Search ...................... 604/96, 101, 54, 48, 604/49; 128/344, 325; 606/191, 192

[56] References Cited

U.S. PATENT DOCUMENTS

| 2,799,273 | 7/1957 | Oddo |  |
|---|---|---|---|
| 2,936,760 | 5/1960 | Gants | 604/101 |
| 4,456,011 | 6/1984 | Warnecke | 128/325 |
| 4,573,966 | 3/1986 | Weiki et al. | 604/53 |
| 4,610,662 | 9/1986 | Weiki et al. | 604/53 |
| 4,636,195 | 1/1987 | Wolinsky | 604/53 |
| 4,637,396 | 1/1987 | Cook | 128/344 |
| 4,660,560 | 4/1987 | Klein | 128/344 |
| 4,702,252 | 10/1987 | Brooks et al. | 128/344 |
| 4,705,502 | 11/1987 | Patel | 604/101 |

FOREIGN PATENT DOCUMENTS 3425437 1/1986 Fed. Rep. of Germany .

OTHER PUBLICATIONS

Deisting, W., Urol. internation, 2, 158–171 (1956).

Primary Examiner—Stephen C. Pellegrino
Attorney, Agent, or Firm—Peter C. Richardson; Lawrence C. Akers; Mark Dryer

[57] ABSTRACT

An apparatus for dilation of the prostate urethra comprises a urinary catheter for insertion in the prostate urethra, dilation means mounted on the proximal section of the catheter and in communication with the interior of the catheter, location means mounted axially on the catheter at a distance from the dilation means such that the location means is at the bulbous urethra when the dilation means is at the prostate urethra, and activating means for activating said dilation means and said location means. A method for the treatment of benign prostatic hyperplasia comprises inserting a urinary catheter having dilation means and location means and removing the catheter after dilation.

15 Claims, 3 Drawing Sheets

PROSTATE BALLOON DILATOR

BACKGROUND OF THE INVENTION

The invention relates to a catheter having inflatable means for dilation of the prostate urethra, and to a method for the treatment of benign prostatic hyperplasia.

Balloon catheters are widely used for dilation of undesirable tissue in body vessels. For instance, U.S. Pat. No. 4,636,195 discloses removal of constrictions caused by deposition of plaque in arteries by a balloon catheter. The disclosed catheter has two smaller ring balloons spaced around a central dilation balloon. The smaller ring balloons provide a chamber around a body of plaque, and help to hold the catheter body in place. Other multiple balloon catheters are disclosed in U.S. Pat. Nos. 4,573,966 and 4,610,662, both assigned to Schneider Medintag A.G. The two balloons of these catheters are placed in a vascular passageway to seal off a constricted area, and dissolving fluid is supplied to the enclosed area to dissolve the constrictive tissue.

Treatment of obstructive tissue in the prostate urethra with a balloon catheter is disclosed in Klein U.S. Pat. No. 4,660,560. Klein describes a catheter having a Foley balloon for anchoring the catheter by inflation within the bladder, and an annular balloon for dilation of the prostate urethra. Klein attains proper location of the annular balloon by introducing a cystoscope into the prostate urethra. The operation of the cystoscope to determine the location of the prostate urethra with respect to the bladder neck is cumbersome, and can be avoided by the invention as described below.

SUMMARY OF THE INVENTION

An apparatus for dilation of the prostate urethra comprises a catheter for insertion in the prostate urethra, said catheter having proximal section and a distal section; a dilation means is mounted on said proximal section of the catheter for dilating the prostate urethra location means mounted on the catheter at distance from the dilation means such that the location balloon is positioned at and fits in the bulbous urethra distal from the external sphincter to hold the catheter in place when the dilation means is positioned at the prostate urethra; and actuating means located at said distal section of the catheter for activating said dilation means and said location means.

In a preferred embodiment of the invention, the dilation means is a dilation balloon and the location means is a location balloon.

The dilation balloon is preferably made of a limited distensible material such that the balloon can not expand from its initial deflation diameter to substantially beyond a predetermined diameter regardless of the internal pressure applied to the balloon.

A method for the treatment of benign prostatic hyperplasia comprises inserting into a prostate urethra an urinary catheter having dilation means for dilating the prostate urethra and location means for location of the dilation means at the prostate urethra, locating and fixing said location means, placing and dilating said dilation means and thereby, dilating the prostate urethra with said dilation means to alleviate obstruction of the prostate urethra resulting from benign prostatic hyperplasia, deactivating said dilation means and location means, and removing said catheter from said prostate urethra.

In said method the dilation means is preferably a dilation balloon and the location means is preferably a location balloon.

DETAILED DESCRIPTION OF THE INVENTION

Figure 1:
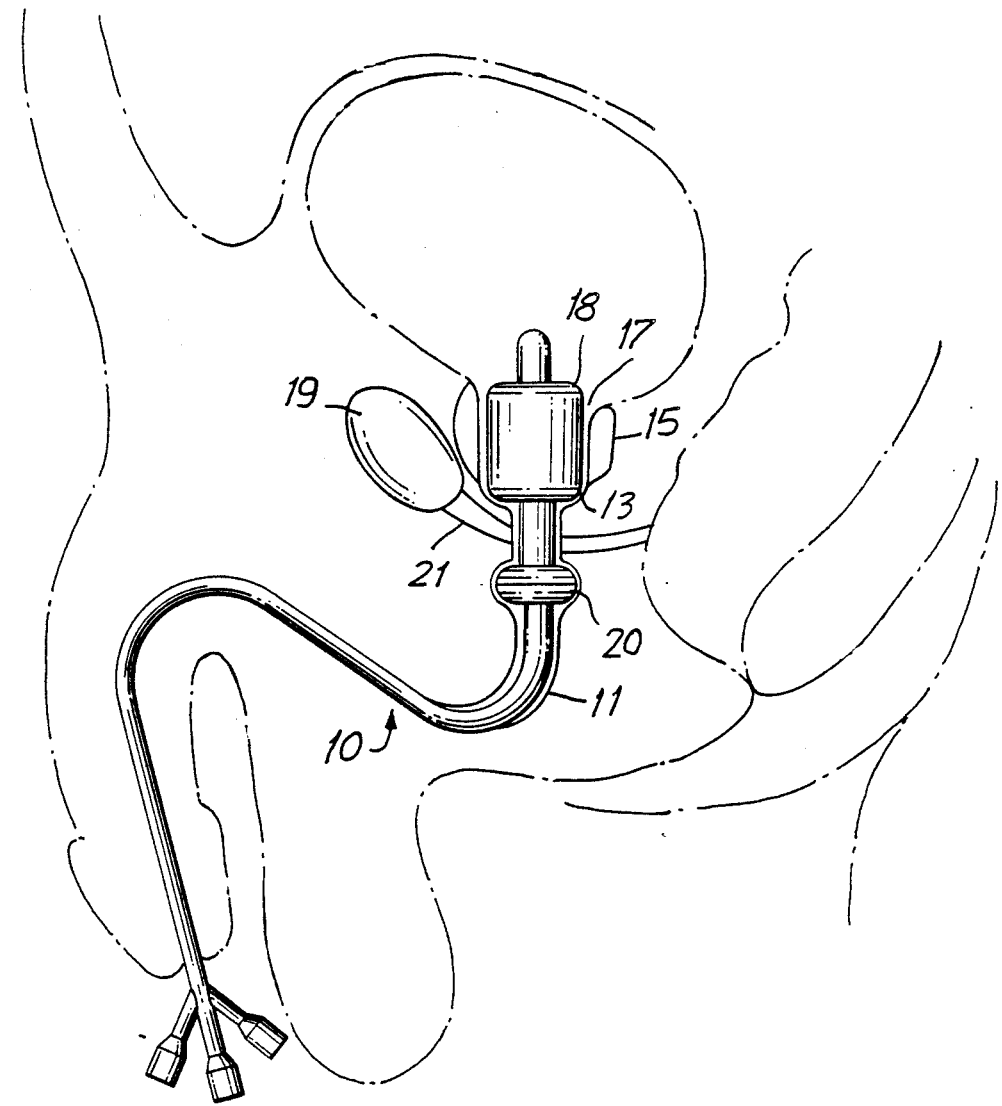
FIG. 1 illustrates a dual balloon catheter according to the invention as it is inserted in the male urethra, showing the balloons in inflated condition.

FIG. 1 illustrates dual balloon catheter 10 of the present invention positioned within the male urethra 11. Inflatable location balloon 20 located at the bulbous urethra anchors the device 10 in place and secures it against significant movement in the longitudinal directions, particularly in the direction of the bladder. Inflatable dilation balloon 18 is located at the prostate urethra 13 near the prostate 15 and extends into the bladder neck 17. FIG. 1 shows the location of the male urethra relative to the pubic bone 19 and the urogenital diaphragm (or pelvic floor) 21.

Figure 2:
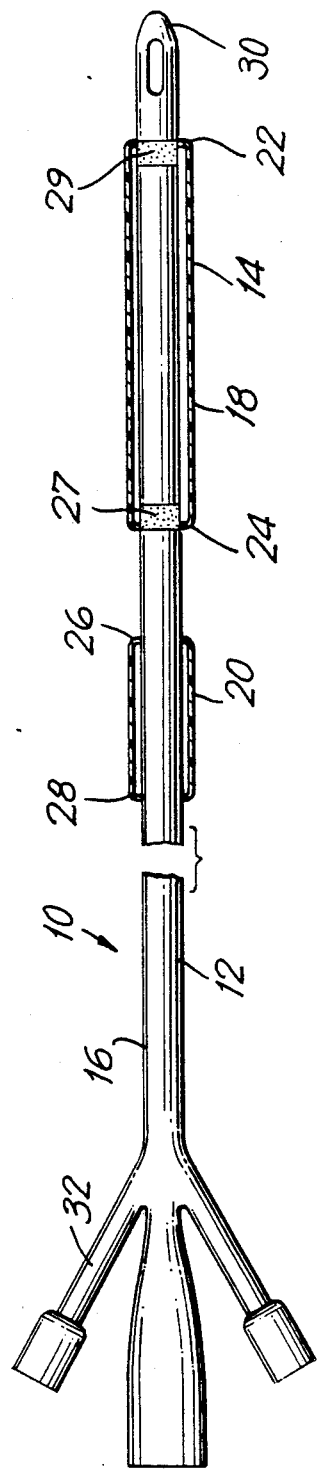
FIG. 2 is a fragmentary sectional view of the device of FIG. 1.

FIG. 2 shows the device 10 comprising catheter tube 12 having proximal section 14 for location toward the center of the body on proper insertion of the device 10 in the body, and distal section 16 for location away from the center of the body on proper insertion of the device 10 in the body.

The catheter tube 12 is formed of a material which is flexible enough to follow the bends in the urethra on insertion of the device 10. The material should be rigid enough, however, to allow the device 10 to pass over any obstructions within the urethra on insertion of the device 10. The catheter tube is composed of or covered by a biocompatible material to avoid irritations and complications in the urethra. Suitable biocompatible materials which can be made into tubing of suitable flexibility and rigidity are silicone, polyester, polyvinylchloride, and polyurethane.

Mounted on the proximal section 14 is axial dilation balloon 18 and axial location balloon 20. Dilation balloon 18 is in communication with the interior of catheter tube 12, as described in more detail with reference to FIG. 3. Dilation balloon 18 may be replaced by multiple balloons, although one dilation balloon is preferred. The location balloon 20 is at a distance from dilation balloon 18 such that location balloon 20 is at the bulbous urethra when the dilation balloon 18 is at the prostate urethra.

Balloons 18 and 20 are formed of a biocompatible material such as silicone elastomer, polyvinylchloride, polyester, natural or synthetic rubber, or polyurethane. Dilation balloon 18 in general is made such that it does not expand beyond a predetermined diameter. Such limited expansion of the balloon 18 prevents overdilation and thus prevents damage to the prostate urethra during dilation. In one embodiment, the limited expansion is attained by making the dilation balloon of a non-distensible material such as polyvinylchloride, polyethylene terephthalate, or polyethylene. In the deflated state, such non-distensible balloon is in a folded configuration. Such limited expansion, alternatively, may be attained by making the balloon 18 of a limited distensible composite material as defined above. Multi-layer limited distensible materials of use in the present invention are described in Cook U.S. Pat. No. 4,637,396 with respect to dilation "balloon 12" having a three layer wall. The inner layer is an elastic impervious polyurethane membrane, the middle layer is a knitted fabric tube, and the outer layer is an elastic impervious polyurethane membrane. Other multi-layer limited distensible materials of use in the present invention are the bistable materials described in U.S. Pat. No. 4,651,721, the disclosure of which is incorporated by reference. The limited distensible material may be part of a three layer composite having an outer layer which is elastic and may be formed of silicone elastomer, a middle layer of a bistable material such as polyester/polyurethane fabric, and an inner layer which is elastic and impervious and may be formed of silicone elastomer. The bistable material may be a fabric made of yarns composed of non-distensible fibers such as polyester fibers and distensible fibers such as polyurethane fibers. The distensible fibers allow for collapse of the balloon to about the outer diameter of the catheter tube 12, and the non-distensible fibers allow for inflation of the balloon to the predetermined diameter.

The predetermined diameter of the dilation balloon 18 is generally about 25 mm to about 40 mm.

The dilation balloon 18 has a proximal end 22 and a distal end 24, and the location balloon 20 has a proximal end 26 and a distal end 28. The distance between the distal end 24 of the dilation balloon 18 and the proximal end 26 of the location balloon 20 varies with the relative location of the prostate urethra and the bulbous urethra in a patient, and is usually from about 1 cm to about 4 cm, most typically 1 cm. The device 10 has a proximal end 30 and a distal end 32. The proximal end 22 of the dilation balloon 18 is usually about 1 cm to about 3 cm from the proximal end 30 of the device 10. Optionally, the dilation balloon extends beyond the proximal end 30.

The length of the dilation balloon 18, that is the distance between the proximal end 22 and the distal end 24, depends on the size of the prostate urethra of a patient. In general, such length of balloon 18 is about 3 cm to about 6 cm, commonly 4 cm, in accordance with the general size of a male prostate urethra. The dilation balloon 18 may extend beyond the prostate urethra into the bladder neck, so allowing for some flexibility in use of a limited number of lengths of dilation balloons for different lengths of prostate urethras.

The length of the location balloon 20, that is the distance between the proximal end 26 and the distal end 28, is such that the balloon fits in the bulbous urethra of a patient. The balloon 20 need not occupy the entire space of the bulbous urethra. The functions of the balloon 20 are locating the prostate urethra, and fixating the device 10 against movement within the urethra, particularly against movement in the direction of the bladder. As a general rule, the length of the location balloon 20 is about 1 cm to 6 cm.

Radiopaque markers 27 and 29 are conveniently used to guide fluoroscopy examination.

Figure 3:
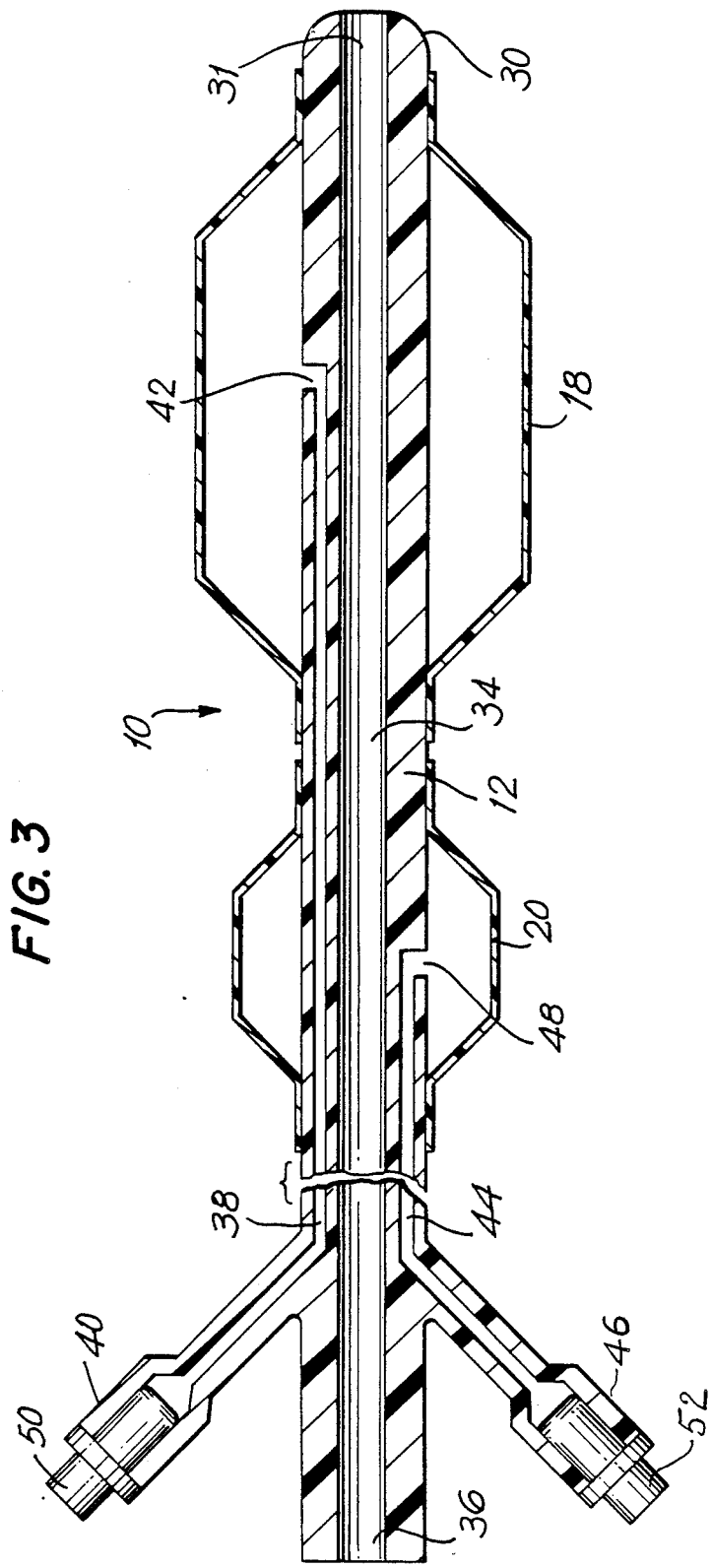
FIG. 3 is a cross-sectional view of the device of FIG. 1 showing the balloons in inflated condition.

FIG. 3 shows one embodiment of the dilation balloon 18, as attached to catheter tube 12. Drainage lumen 34 extends from the opening 31 at proximal end 30 through the catheter tube 12 to bladder drainage hole 36. The drainage lumen is an optional feature of device 10. A dilation lumen 38 communicates between a dilation balloon fill port 40 and the dilation balloon 18 through a dilation balloon opening 42. An inflation lumen 44 communicates between a location balloon fill port 46 and the location balloon 20 through a location balloon opening 48. Each of balloon fill ports 40 and 46 have a catheter valve or syringe fitting 50 and 52, respectively, to allow for connection of the fill ports with syringes for injection of fluid.

OPERATION

Before insertion into the urethra, device 10 is in a completely deflated state such that balloons 18 and 20 are collapsed against the exterior of catheter tube 12.

The device 10 is guided into and along the urethra. To facilitate insertion, the device 10 may be guided over a previously inserted guide wire or the drainage lumen 34 may contain a guide wire so increasing the stiffness of the device 10.

The location balloon 20 is properly located at the bulbous urethra. The doctor feels the bulbous urethra by rectal palpation or determines the position of the bulbous urethra by other means such as fluoroscopic guidance. Conveniently, the location balloon 20 is inflated to at least some extent when it is in the vicinity of the bulbous urethra as determined by the doctor by rectal palpation or other known means. The location balloon 20 is inflated to its full extent after location at the bulbous urethra.

For inflation of the balloon 20, the inflation lumen 44 leading to the location balloon 20 is connected to an inflating means such as a syringe, and inflation fluid is injected to inflate balloon 20 by fluid pressure. The inflation fluid is preferably a radiopaque fluid for taking of post insertion X-ray, and viewing of the device while in the body. Hypaque-25 and Renografin-60 are examples of suitable radiopaque fluids. Sufficient fluid is injected to secure the device 10 in its proper position. Once the inflated location balloon 20 is properly located at the bulbous urethra distal from the external sphincter, the doctor knows that the dilation balloon 18 is at its proper location at the prostate urethra since the location balloon 20 of device 10 is at a distance from the dilation balloon 18 such that when location balloon 20 is at the bulbous urethra then the dilation balloon 18 is at the prostate urethra. In this manner, dilation of the external sphincter and the possible harmful effects of such dilation is avoided.

The dilation balloon 18 is now connected to a pressure gauge through the dilation lumen 38, and inflated. The proper inflation pressure for maximum dilation is attained by injecting a volume of fluid equal to the predetermined capacity of balloon 18, or by determining the maximum pressure on the pressure gauge when exerting pressure on the balloon 18. As is known in the dilation art in general, fluoroscopy aids in visualizing the extent of the balloon's expansion and in monitoring the dilation procedure.

In the preferred embodiment when the dilation balloon 18 is made of limited distensible material as described above, the balloon 18 expands to its predetermined maximum diameter.

After dilation, balloons 18 and 20 are deflated, and the device 10 is removed.

We claim:

1. An apparatus for dilation of the prostate urethra comprising:

a urinary catheter for insertion in the prostate urethra, said catheter having a proximal section and a distal section;

dilation means mounted on said proximal section of the catheter for dilating the prostate urethra;

location means mounted on the catheter at a distance from the dilation means such that the location means is positioned at and fits in the bulbous urethra distal from the external sphincter when the dilation means is positioned at the prostate urethral; and activating means located at said distal section of the catheter for activating said dilation means and said location means, and thereby holding the catheter in place when said dilation means and said location means are activated.

2. An apparatus according to claim 1 wherein said dilation means is a dilation balloon and said location means is a location balloon.

3. An apparatus according to claim 2 wherein said dilation balloon is made of a multi-layer limited distensible material.

4. An apparatus according to claim 3 wherein said multi-layer limited distensible material comprises an inner and outer layer of silicone and a middle layer of a limited distensible fabric.

5. An apparatus according to claim 2 wherein said dilation balloon and said location balloon each have a proximal end and a distal end, and the distal end of the dilation balloon is at a distance of about 1 to about 4 centimeter from the proximal end of the location balloon.

6. An apparatus according to claim 2 wherein said dilation balloon and said catheter each have a proximal end and a distal end, and said proximal end of the dilation balloon is at a distance of about 1 to about 3 centimeter from said proximal end of the catheter.

7. An apparatus according to claim 5 wherein the distance between said proximal end and said distal end of the dilation balloon is about 3 to about 6 centimeter.

8. An apparatus according to claim 2 wherein said catheter has three lumens extending from said proximal section, one lumen in communication with said dilation balloon, one lumen in communication with said location balloon, and one lumen adapted for communication with the bladder of a subject.

9. A method for the treatment of benign prostatic hyperplasia which comprises:

inserting into a prostate urethra a hollow, impervious, urinary catheter having dilation means for dilating the prostate urethra and location means for locating the dilation means at the prostate urethra;

locating and fixing said location means; placing and dilating said dilation means and thereby dilating the prostate urethra with said dilation means to alleviate obstruction of the prostate urethra resulting from benign prostatic hyperplasia;

deactivating said dilation means and location means, and removing said catheter from said prostate urethra.

10. A method according to claim 9 wherein said dilation means is a dilation balloon and said location means is a location balloon.

11. A method according to claim 10 wherein said location balloon is axially mounted on said catheter at a distance from said dilation balloon such that when the dilation balloon is positioned at the prostate urethra then the location balloon is positioned at the bulbous urethra distal from the external sphincter, and said location balloon on inflation is sized to fit in the bulbous urethra.

12. A method according to claim 11 wherein after insertion of the catheter, the location balloon is inflated first before inflation of the dilation balloon.

13. A method according to claim 10 wherein liquid is circulated through said dilation balloon.

14. A method according to claim 10 wherein said dilation balloon is made of a multi layer limited distensible material.

15. A method according to claim 10 wherein said dilation balloon is axially mounted on said catheter.

* * * * *